United States Patent
Hill (10) Patent No.: US 11,534,175 B2
(45) Date of Patent: Dec. 27, 2022

(54) MODULAR LEFT ATRIAL APPENDAGE CLOSURE

(71) Applicant: Medtronic, Inc., Minneapolis, MN (US)

(72) Inventor: Alexander Hill, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 87 days.

(21) Appl. No.: 16/774,394

(22) Filed: Jan. 28, 2020

(65) Prior Publication Data
US 2021/0228215 A1 Jul. 29, 2021

(51) Int. Cl.
*A61B 17/12* (2006.01)

(52) U.S. Cl.
CPC ............ *A61B 17/12122* (2013.01); *A61B 17/12031* (2013.01); *A61B 17/12172* (2013.01)

(58) Field of Classification Search
CPC ........ A61B 17/12122; A61B 17/12172; A61B 17/12031; A61B 17/12163; A61B 17/12159
See application file for complete search history.

(56) References Cited

U.S. PATENT DOCUMENTS

| | | |
|---|---|---|
| 8,308,759 B2 | 11/2012 | Olsen et al. |
| 8,409,219 B2 | 4/2013 | Kelley et al. |
| 9,474,517 B2 | 10/2016 | Amin et al. |
| 9,656,063 B2 | 5/2017 | Kelley et al. |
| 9,808,253 B2 | 11/2017 | Li et al. |
| 9,943,315 B2 | 4/2018 | Kaplan et al. |
| 2004/0122467 A1* | 6/2004 | VanTassel ........ A61B 17/12136 606/200 |
| 2008/0015635 A1 | 1/2008 | Olsen et al. |
| 2008/0015636 A1 | 1/2008 | Olsen et al. |
| 2008/0215086 A1 | 9/2008 | Olsen et al. |

(Continued)

FOREIGN PATENT DOCUMENTS

| | | |
|---|---|---|
| DE | 102015004535 A1 | 10/2016 |
| EP | 3398536 A1 | 11/2018 |
| WO | 0130266 A1 | 5/2001 |

OTHER PUBLICATIONS

International Search Report and Written Opinion dated May 3, 2021, for corresponding International Application No. PCT/US2021/012043; International Filing Date: Jan. 4, 2021 consisting of 13-pages.

*Primary Examiner* — Katherine H Schwiker
*Assistant Examiner* — Raihan R Khandker
(74) *Attorney, Agent, or Firm* — Michael Best & Friedrich LLP (57) ABSTRACT

Devices, methods, and systems for closure device for a left atrial appendage and, in particular, to a closure device that includes an anchor element and a disc element that are each individually chosen based on the anatomy of the patient's left atrial appendage and assembled before implantation. In one embodiment, a medical device comprises: an anchor element, the anchor element including a first connection element; and a disc element, the disc element including a second connection element pivotably coupled to the first connection element, the anchor element being sized to be received and retained within a left atrial appendage and the disc element being sized to completely cover an opening of the left atrial appendage.

20 Claims, 7 Drawing Sheets

(56) References Cited

U.S. PATENT DOCUMENTS

| | | |
|---|---|---|
| 2010/0042110 A1 | 2/2010 | Kelley et al. |
| 2011/0022080 A1 | 1/2011 | Olsen et al. |
| 2012/0172927 A1* | 7/2012 | Campbell ........ A61B 17/12172 606/213 |
| 2013/0165967 A1 | 6/2013 | Amin et al. |
| 2013/0190811 A1 | 7/2013 | Olsen et al. |
| 2013/0296880 A1 | 11/2013 | Kelley et al. |
| 2014/0046347 A1* | 2/2014 | Cully ............... A61B 17/12168 606/151 |
| 2014/0142612 A1 | 5/2014 | Li et al. |
| 2014/0277074 A1 | 9/2014 | Kaplan et al. |
| 2015/0250482 A1 | 9/2015 | Slaughter et al. |
| 2016/0100844 A1 | 4/2016 | Li et al. |
| 2016/0213358 A1 | 7/2016 | Amin et al. |
| 2016/0278749 A1 | 9/2016 | Javois et al. |
| 2017/0035435 A1 | 2/2017 | Amin et al. |
| 2017/0042549 A1 | 2/2017 | Kaplan et al. |
| 2017/0281330 A1* | 10/2017 | Liljegren .................. A61F 2/04 |
| 2018/0000490 A1 | 1/2018 | Kaplan et al. |
| 2018/0235640 A1 | 8/2018 | Slaughter et al. |
| 2018/0250014 A1 | 9/2018 | Melanson et al. |
| 2018/0360432 A1* | 12/2018 | Corcoran ............... A61M 29/00 |
| 2019/0110796 A1* | 4/2019 | Jayaraman ........ A61B 17/12168 |
| 2020/0054343 A1* | 2/2020 | Min .................. A61B 17/12136 |
| 2020/0390428 A1* | 12/2020 | Lee .................. A61B 17/12163 |

\* cited by examiner

MODULAR LEFT ATRIAL APPENDAGE CLOSURE

CROSS-REFERENCE TO RELATED APPLICATION n/a

FIELD

The present technology relates, in general, to a closure device for a left atrial appendage and, in particular, to a closure device that includes an anchor element and a disc element that are each individually chosen based on the anatomy of the patient's left atrial appendage and assembled before implantation.

BACKGROUND

Atrial fibrillation (AF) is a condition in which irregular heartbeats are caused by the propagation of disorganized electrical signals within cardiac tissue. Patients with AF, particular patients with non-valvular AF, are five times more likely of having a stroke than patients without AF. This increased risk is believed to originate from the left atrial appendage (LAA), a muscular pouch within the pericardium that opens into the left atrium of the heart. The structure of the LAA, such as muscular ridges and folds formed on the interior surface of the LAA and the LAA's comparatively small size, is conducive to blood pooling and stagnation within the LAA and, consequently, the formation of blood clots. Additionally, in AF the heart beats rapidly and often with less force, which may not allow the LAA to adequately receive and expel fresh blood from within. If a blood clot escapes the LAA and enters the left atrium to be circulated throughout the body, there is a risk that the clot will cause an embolism and stroke.

Consequently, it is believed that preventing the passage of clots from the LAA into the left atrium may significantly reduce the likelihood of stroke, particularly in patients with AF. Procedures for preventing clot movement from the LAA include removal of the LAA, ligation or closure of the LAA, implanting a device within the LAA that prevents the flow of blood into and out of the LAA, and implanting a device within the LAA that functions as a filter to allow the flow of blood therethrough but prevent the movement of larger particles, such as clots, from exiting the LAA. Additionally, drug therapy (for example, with blood-thinning drugs) may be used to reduce the risk of stroke in patients with AF.

However, not all patients can tolerate drug therapy. Also, removal and ligation of the LAA typically are major procedures that require opening of the chest cavity and long recovery time, as well as an increased risk for infection, trauma, and adverse reactions to anesthesia. Not only are such procedures expensive, but they are painful as well.

Many modern implantable devices are configured to be delivered with a catheter in a minimally invasive procedure. This reduces many of the risks presented by procedures such as open heart surgery. However, to function effectively, it is very important that the implantable device be properly positioned relative to the LAA. For example, if the implantable device is not properly seated within the LAA and/or against the opening of the LAA, blood, as well as clots, may still freely flow past the device into and from the LAA, rendering the device ineffective. Some implantable devices include both an anchor portion that is configured to be received within the LAA and a disk portion that is attached to the anchor portion and configured to be seated against the opening of the LAA. The LAA is a morphologically diverse structure, with the size and shape varying widely between individuals. Although some of these devices are made in a variety of sizes, even this does not provide full occlusion in all patients.

SUMMARY

The techniques of this disclosure relate, in general, to a closure device for a left atrial appendage and, in particular, to a closure device that includes an anchor element and a disc element that are each individually chosen based on the anatomy of the patient's left atrial appendage and assembled before implantation. In one embodiment, a medical device comprises: an anchor element, the anchor element including a first connection element; and a disc element, the disc element including a second connection element pivotably coupled to the first connection element, the anchor element being sized to be received and retained within a left atrial appendage and the disc element being sized to completely cover an opening of the left atrial appendage.

In one aspect of the embodiment, the first connection element is a ball and the second connection element is a socket that is configured to receive and retain at least a portion of the ball.

In one aspect of the embodiment, the anchor element is a self-expanding frame.

In one aspect of the embodiment, the self-expanding frame includes at least one of a mesh and a plurality of arms.

In one aspect of the embodiment, the self-expanding frame includes a plurality of arms and a mesh at least partially surrounding the plurality of arms.

In one aspect of the embodiment, the self-expanding frame is composed of a shape memory material.

In one aspect of the embodiment, the anchor element includes: an expandable frame; and an inflatable element within the expandable frame.

In one aspect of the embodiment, inflation of the inflatable element expands the expandable frame.

In one aspect of the embodiment, the expandable frame includes at least one of a mesh and a plurality of arms.

In one aspect of the embodiment, the expandable frame is composed of a shape memory material.

In one aspect of the embodiment, the disc element is composed of a shape memory material.

In one aspect of the embodiment, the disc element is composed of a resilient and flexible material.

In one aspect of the embodiment, the disc element includes a threaded engagement element.

In one embodiment, a system for a left atrial appendage comprises: a modular closure device, the modular closure device including: an anchor element, the anchor element including a ball connected to the anchor element by a post, the anchor element including a self-expanding frame composed of a shape memory material; and a disc element, the disc element including a socket that is pivotably couplable to the ball of the anchor element and an engagement element, the disc element being composed of a shape memory material, the anchor element being sized to be received and retained within a left atrial appendage and the disc element being sized to completely cover an opening of the left atrial appendage; and a delivery device, the delivery device including a push rod that is removably couplable to the engagement element of the disc element. In one aspect of the embodiment, the self-expanding frame includes a plurality of arms and a mesh covering at least a portion of the plurality of arms.

In one embodiment, a method for implanting a modular closure device within a left atrial appendage comprises: selecting an anchor element based on the size and configuration of the left atrial appendage of a patient, the anchor element including a first connection element; selecting a disc element based on the size and configuration of an opening of the left atrial appendage of the patient, the disc element including a second connection element; coupling the first connection element of the anchor element to the second connection element of the disc element to assemble the modular closure device; and compressing the modular closure device and inserting the modular closure device into a delivery device.

In one aspect of the embodiment, the method further comprises: inserting a distal end of the delivery device within the left atrial appendage; advancing the modular closure device out of the distal end of the delivery device until the anchor element is distal to the distal end of the delivery device; expanding the anchor element within the left atrial appendage such that at least a portion of the anchor element is in contact with an internal surface of the left atrial appendage; advancing the modular closure device out of the distal end of the delivery device until the disc element is distal to the distal end of the delivery device; and expanding the disc element such that the disc element has an outer diameter that is greater than a largest diameter of an opening of the left atrial appendage.

In one aspect of the embodiment, the anchor element includes a self-expanding frame composed of a shape memory material, and expanding the anchor element includes allowing the self-expanding expanding frame to return to a programmed shape after compression.

In one aspect of the embodiment, the anchor element includes an expandable frame and an inflatable element within the expandable frame, and expanding the anchor element includes inflating the inflatable element to expand the expandable frame.

In one aspect of the embodiment, the disc element is composed of a shape memory material, and expanding the disc element includes allowing the disc element to return to a programmed shape after compression.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
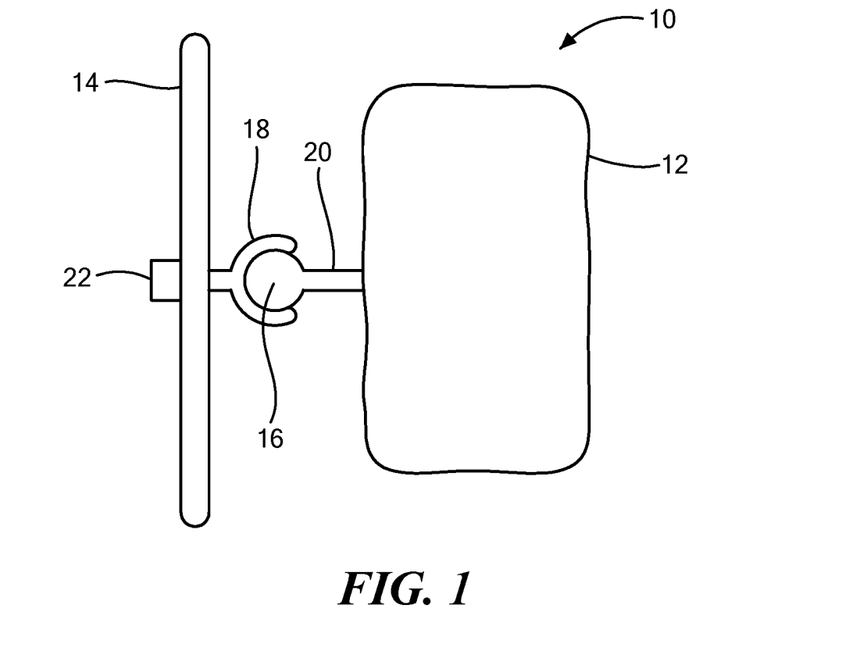
FIG. 1 is a cross-sectional side view of a stylized modular closure device for a left atrial appendage in accordance with the present disclosure.

The present invention provides a left atrial appendage modular closure device including an anchor element and a disc element that are individually selected based on size and anatomy of a left atrial appendage of a patient. Referring to the drawing figures in which like reference designations refer to like elements, FIG. 1 shows a cross-sectional view of an exemplary embodiment of a modular closure device 10 for a left atrial appendage (LAA). The modular closure device 10 generally includes an anchor element 12 and a disc element 14. In one embodiment, the anchor element 12 is configured to be located within the LAA and the disc element 14 is configured to be seated against the opening of the LAA when the modular closure device 10 has been implanted within a patient.

Figure 2:
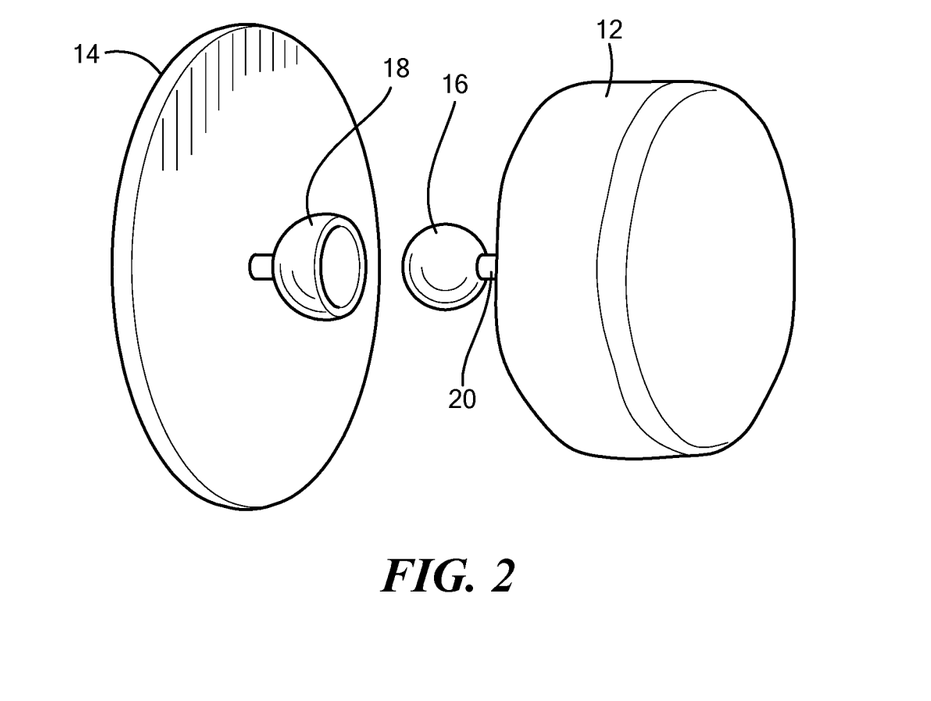
FIG. 2 is a perspective view of the modular closure device of FIG. 1 in accordance with the present disclosure, with the anchor element and the disc element being separated.

Referring to FIGS. 1 and 2, each of the anchor element 12 and the disc element 14 include a connection element. In one embodiment, the anchor element 12 includes a ball or knob 16 and the disc element 14 includes a socket 18 that is sized and configured to matingly receive and retain at least a portion of the ball 16, thereby coupling the anchor element 12 and the disc element 14 together while allowing movement of the ball 16 within the socket 18 and, therefore, movement or pivoting of the anchor element 12 and the disc element 14 relative to each other. In one embodiment, the anchor element 12 includes a post 20 that extends from a surface of the anchor element 12, and the ball 16 is coupled to or integrated with a free end of the post 20. In one embodiment, the anchor element 12 and the disc element 14 are removably coupled to each other by the ball 16 and socket 18. In another embodiment, the anchor element 12 and the disc element 14 are permanently coupled to each other by the ball 16 and socket 18. In one embodiment, the disc element 14 includes an engagement element 22, such as for removably coupling the disc element 14 (and, therefore, the modular closure device 10) to a push rod or guidewire used for implantation of the modular closure device 10 within the LAA (for example, as seen in FIGS. 7-10). In one embodiment, the engagement element 22 is on a first surface of the disc element 14 and the socket 18 is on a second surface of the disc element 14 that is opposite the first surface.

Continuing to refer to FIGS. 1 and 2, in one embodiment the anchor element 12 and the disc element 14 are each chosen individually before the implantation procedure based on the patient's anatomy (that is, size and configuration of the patient's LAA). For example, the structure of the patient's LAA may be imaged using an imaging system (such as with an X-ray system, computer tomography system, or the like). This may ensure that not only is the anchor element 12 properly sized to fit within the LAA and engage the inner surface of the LAA, but also that the disc element 14 is properly sized to cover or span the opening of the LAA without allowing blood to leak from the LAA into the left atrium. Put another way, in one embodiment the disc element 14 has a diameter that is greater than a largest diameter of the LAA opening. Once implanted within the LAA, tissue may grow over portions of the modular closure device, in a process called endothelialization, thereby further securing the modular closure device within the LAA.

Figure 5:
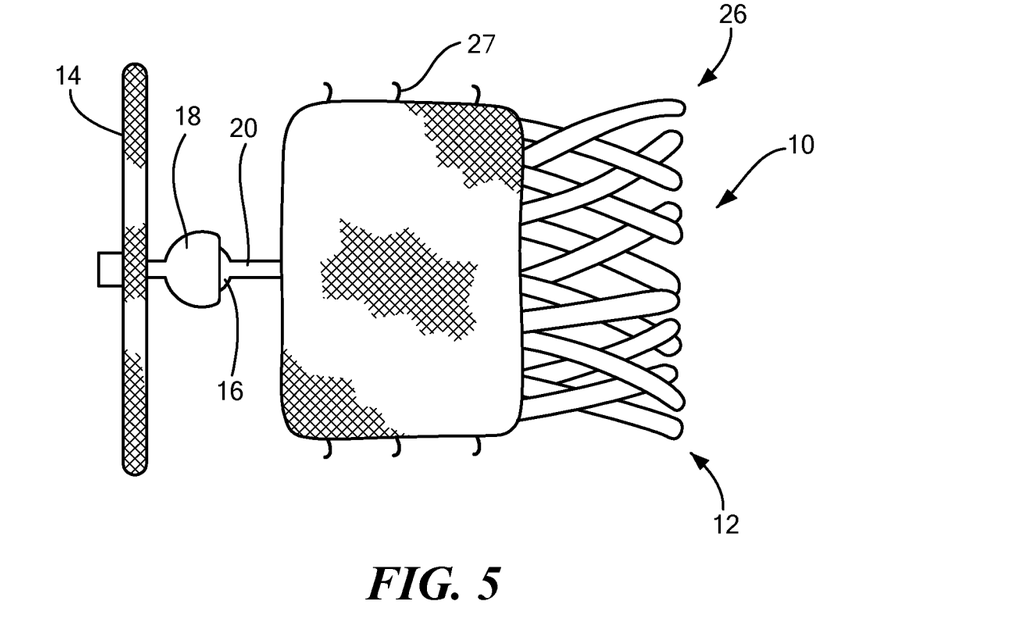
FIG. 5 is a further exemplary embodiment of the anchor element of the modular closure device in accordance with the present disclosure, wherein the anchor element includes a self-expanding frame.
Figure 6:
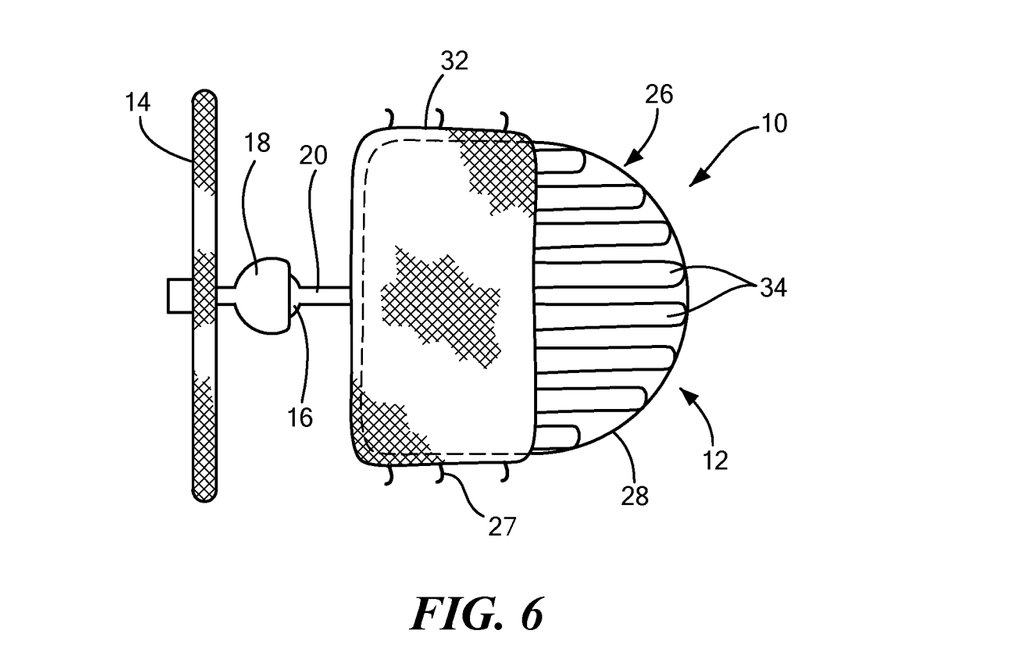
FIG. 6 is a further exemplary embodiment of the anchor element of the modular closure device in accordance with the present disclosure, wherein the anchor element includes an expandable frame and an inflatable element.

Once the appropriate size and/or configuration is determined, the appropriate anchor element 12 and disc element 14 are then coupled to each other by matingly engaging the ball 16 of the anchor element 12 with the socket 18 of the disc element 14. However, it will be understood that in some embodiments the anchor element 12 includes the socket 18 and the disc element 14 includes the ball 16. It will also be understood that connection elements other than those shown and described herein may be used. Once the anchor element 12 and the disc element 14 are coupled together, the modular closure device is compressed to fit into a delivery device 24 (for example, as shown in FIGS. 5 and 6). In one non-limiting example, the delivery device 24 is a delivery sheath or catheter having a size of 14 French.

Figure 3:
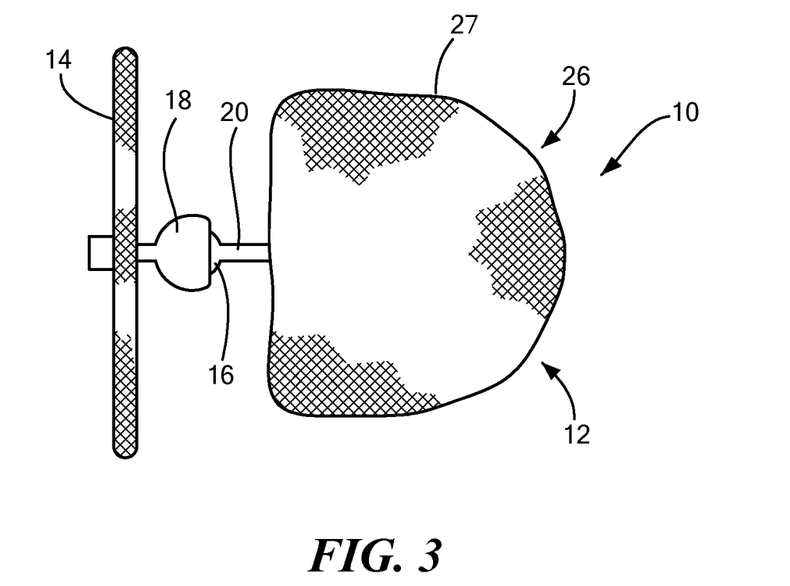
FIG. 3 is an exemplary embodiment of the anchor element of the modular closure device in accordance with the present disclosure, wherein the anchor element includes a self-expanding frame.
Figure 4:
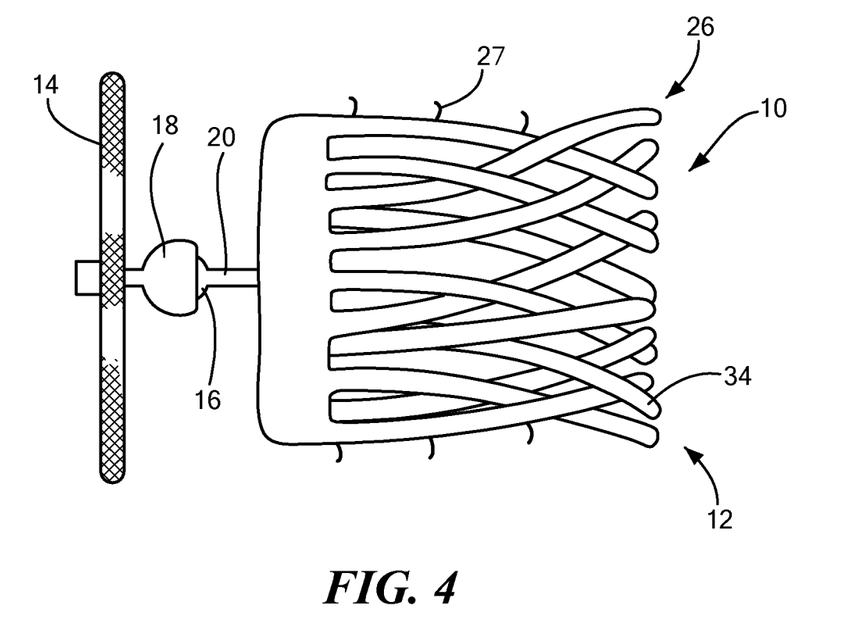
FIG. 4 is a further exemplary embodiment of the anchor element of the modular closure device in accordance with the present disclosure, wherein the anchor element includes a self-expanding frame.

Referring now to FIGS. 3-6, exemplary embodiments of the anchor element 12 are shown. FIGS. 3-5 show exemplary embodiments in which the anchor element includes a self-expanding frame 26 and FIG. 6 shows a further exemplary embodiment in which the anchor element includes an inflatable element 28 within an expandable frame 30. However, it will be understood that the anchor element 12 may have configurations other than those shown and described herein.

Referring now to FIGS. 3-5, in one embodiment the anchor element 12 includes a self-expanding frame 26. In one embodiment, the self-expanding frame 26 is a mesh 32, which may be composed of a mesh, braid, or woven structure of metallic filaments or wires (for example, as shown in FIG. 3). In another embodiment, the self-expanding frame 26 includes a plurality of ribs or arms 34 forming a basket, and the arms 34 may be interconnected at one or more locations along the length of each arm 34. In some embodiments, the self-expanding frame 26 includes both a mesh 32 and plurality of arms 34. For example, the self-expanding frame 26 may include a cage formed by a plurality of arms 34 and a mesh 32 that at least partially surrounds the plurality of arms 43 (as shown in FIG. 5). In these embodiments, the mesh 32 and/or the arms 34 may be composed of a biocompatible shape memory material, such as nitinol, that allows the self-expanding frame 26 to expand to the programmed shape after compression. In some embodiments, the mesh 32 and/or the arms 34 are composed of a flexible and resilient material (in addition to or instead of the shape-memory material) that allows the self-expanding frame 26 to resume a pre-formed shape after compression. When expanded, the anchor element 12 may have any shape or configuration and is not limited to that shown in the figures. Further, the mesh 32 and/or the arms 34 may include one or more prongs, hooks, barbs, or protrusions for engaging tissue within the LAA (not shown). In some embodiments, the disc element 14 is also composed of a shape memory material that is either the same as or different than the shape memory material of the mesh 32 and/or the arms 34. Alternatively, the disc element 14 may be composed of a non-shape-memory material.

Referring now to FIG. 6, in one embodiment the anchor element 12 includes an inflatable element 28 within an expandable frame 30. In one embodiment, the expandable frame 30 is a mesh and/or plurality of arms as discussed above regarding the self-expanding frame 26, and an expandable frame 30 comprising a plurality of arms 34 is shown in FIG. 6 as a non-limiting example. In these embodiments, the mesh 32 and/or the arms 34 may be composed of a flexible and resilient material, such as biocompatible metal or plastic, that allows the expandable frame 30 to expand to a pre-formed shape after compression. Alternatively, the mesh 32 and/or arms 34 may be composed of a flexible and resilient material that has an uncompressed shape defined at least in part by the inflatable element 28 when inflated. In some embodiments, the mesh 32 may be composed of a mesh or woven structure of metallic filaments or wires, woven fabric, mesh of plastic filaments, perforated film of materials such as polypropylene, polyethylene, polyester, or the like. Further, the expandable frame 30 may include one or more prongs, hooks, barbs, or protrusions 27 for engaging tissue within the LAA (not shown). The disc element 14 may be composed of a material that is the same as or different than the material of the mesh 32 and/or the arms 34.

Continuing to refer to FIG. 6, in one embodiment the inflatable element 28 is a balloon or inflatable membrane located within the expandable frame 30. In one embodiment, the inflatable element 28 is a compliant or semi-compliant balloon composed of, for example, Pebax, polyurethane, polytetrafluoroethylene (PTFE), or the like. In one embodiment, the inflatable element 28 is in fluid communication with a source of inflation fluid, such as a gas, gel, or liquid. The modular closure device 10 may be configured such that the inflatable element 28 is left in the LAA within the expandable frame 30. Alternatively, the modular closure device 10 may be configured such that the inflatable element 28 is deflated and removed from the patient after the modular closure device 10 has been implanted. In one non-limiting example, the anchor element 12 and disc element 14, as well as the ball 16, socket 18, and/or post 20, may each include a channel through which the inflatable element 28 may be withdrawn while leaving the modular closure device 10 in place within the LAA.

Referring now to FIGS. 7-10, an exemplary method of delivering and implanting a modular closure device 10 within a LAA 46 is shown. In a first step, as discussed above, an appropriately sized anchor element 12 and disc element 14 are individually chosen based on the unique anatomy of the patient's LAA 46. Once chosen, the anchor element 12 and disc element 14 are coupled to each other using the connection elements (for example, the ball 16 and socket 18 shown in FIGS. 1 and 2) to form the assembled modular closure device 10. The modular closure device 10 is then collapsed, folded, or otherwise compressed to fit within the delivery device 24. Subsequent steps are shown in FIGS. 7-10.

Figure 7:
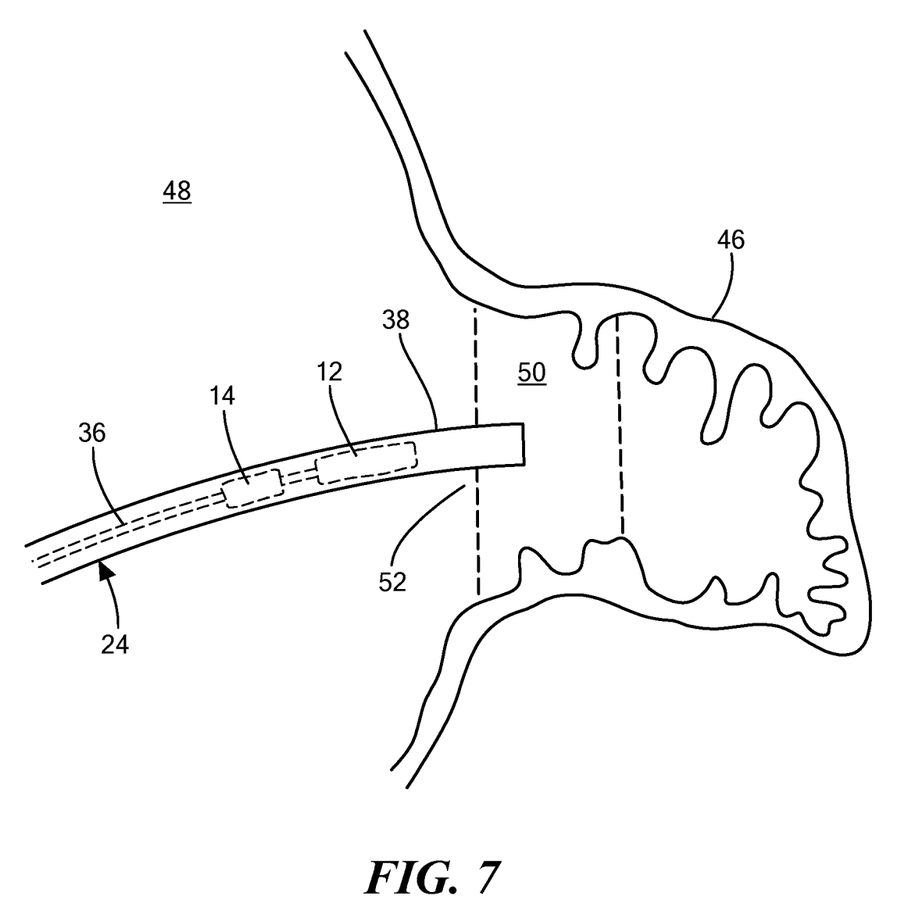
FIG. 7 is a step in delivering the modular closure device to the target site in accordance with the present disclosure, wherein the modular closure device is in a compressed configuration within a delivery device.

Referring now to FIG. 7, the delivery device 24 is navigated through the patient's vasculature and into the left atrium 48 of the heart (such as through a transseptal procedure). The distal end of the delivery device 24 is then positioned proximate or at least partially within the LAA 46, with the distal tip 40 of the delivery device 24 being in the landing zone 50 at or proximate the opening 52 of the LAA 46. As shown in FIG. 7, the modular closure device 10 is compressed and located within the delivery device 24.

Figure 8:
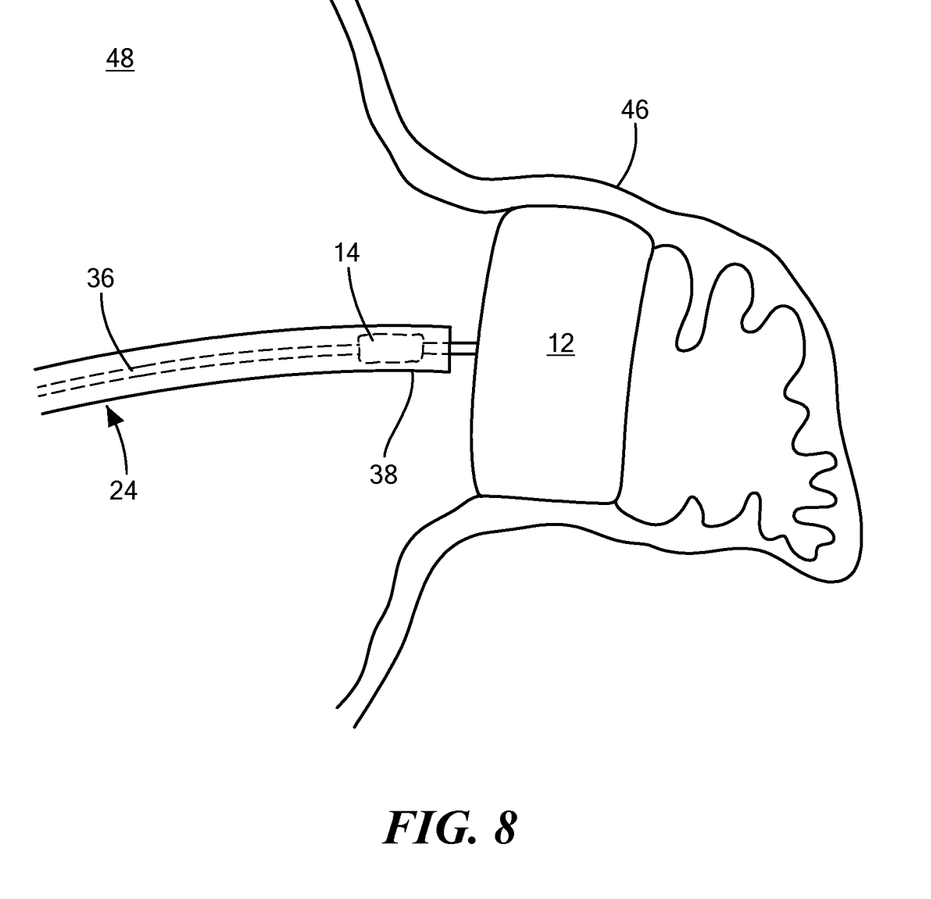
FIG. 8 is a further step in delivering the modular closure device to the target site in accordance with the present disclosure, wherein the modular closure device is at least partially in the compressed configuration and is emerging from the delivery device.
Figure 10:
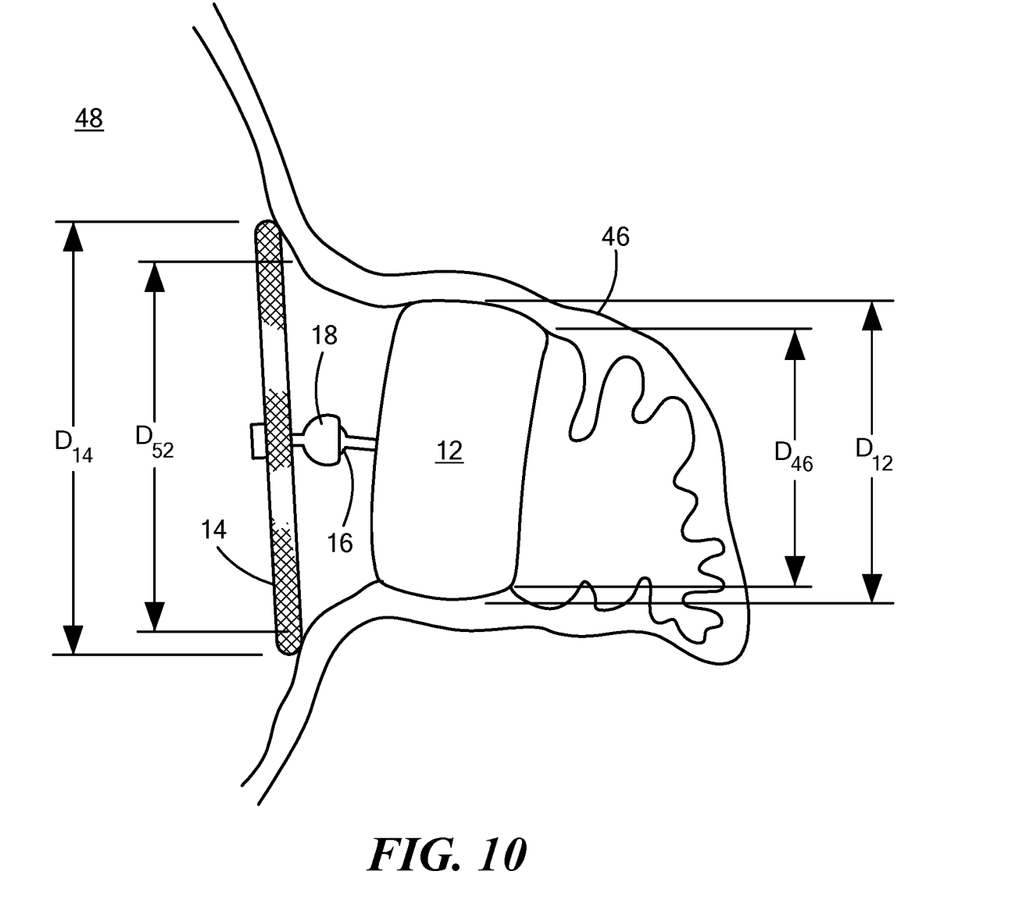
FIG. 10 shows a further step in delivering the modular closure device to the target site in accordance with the present disclosure, wherein the delivery device is disengaged from the modular closure device for removal from the patient's body.

Referring now to FIG. 8, the modular closure device 10 is advanced through delivery device 24 until at least the anchor element 12 exits through an orifice in the distal tip 40 of the delivery device 24. In one embodiment, the modular closure device 10 is removably coupled to a push rod, elongate body, guidewire, or other device to facilitate movement of the modular closure device 10 through the delivery device 24. In embodiments of the anchor element 12 such as those shown in FIGS. 3-5, the anchor element 12 self expands once it is free of the delivery device 24. In one embodiment, the size of the anchor element 12 is chosen such that, when expanded, the self-expanding frame 26 expands to a diameter $D_{12}$ that is greater (or slightly greater) than a diameter $D_{46}$ at least a portion of the LAA 46 that is proximate to the LAA's opening 52 (for example, as shown in FIG. 10). Thus, when the self-expanding frame 26 expands, the mesh 32 and/or arms 34 come into contact with, and may press into, the inner surface of the LAA 46. For example, in some embodiments wherein the mesh 32 and/or arms 34 include barbs or other features, these barbs press into or otherwise engage the inner surface of the LAA 46 to further anchor the anchor element 12 within the LAA 46. In the embodiment shown in FIG. 6, the user expands the inflatable element 28 by delivering an inflation fluid to the interior chamber of the inflatable element 28. Inflation of the inflatable element 28 then serves to expand the expandable frame 30. In one embodiment, the user inflates the inflatable element 28 to a size or outer diameter that will expand the expandable frame 30 to a diameter $D_{12}$ that is greater (or slightly greater) than a diameter $D_{46}$ at least a portion of the LAA 46 that is proximate to the LAA's opening 52. Thus, when the expandable frame 30 expands, the expandable frame 30 (for example, mesh 32 and/or arms 34) come into contact with, and may press into, the inner surface of the LAA 46. For example, in some embodiments wherein the mesh 32 and/or arms 34 include barbs or other features, these barbs press into or otherwise engage the inner surface of the LAA 46 to further anchor the anchor element 12 within the LAA 46.

Figure 9:
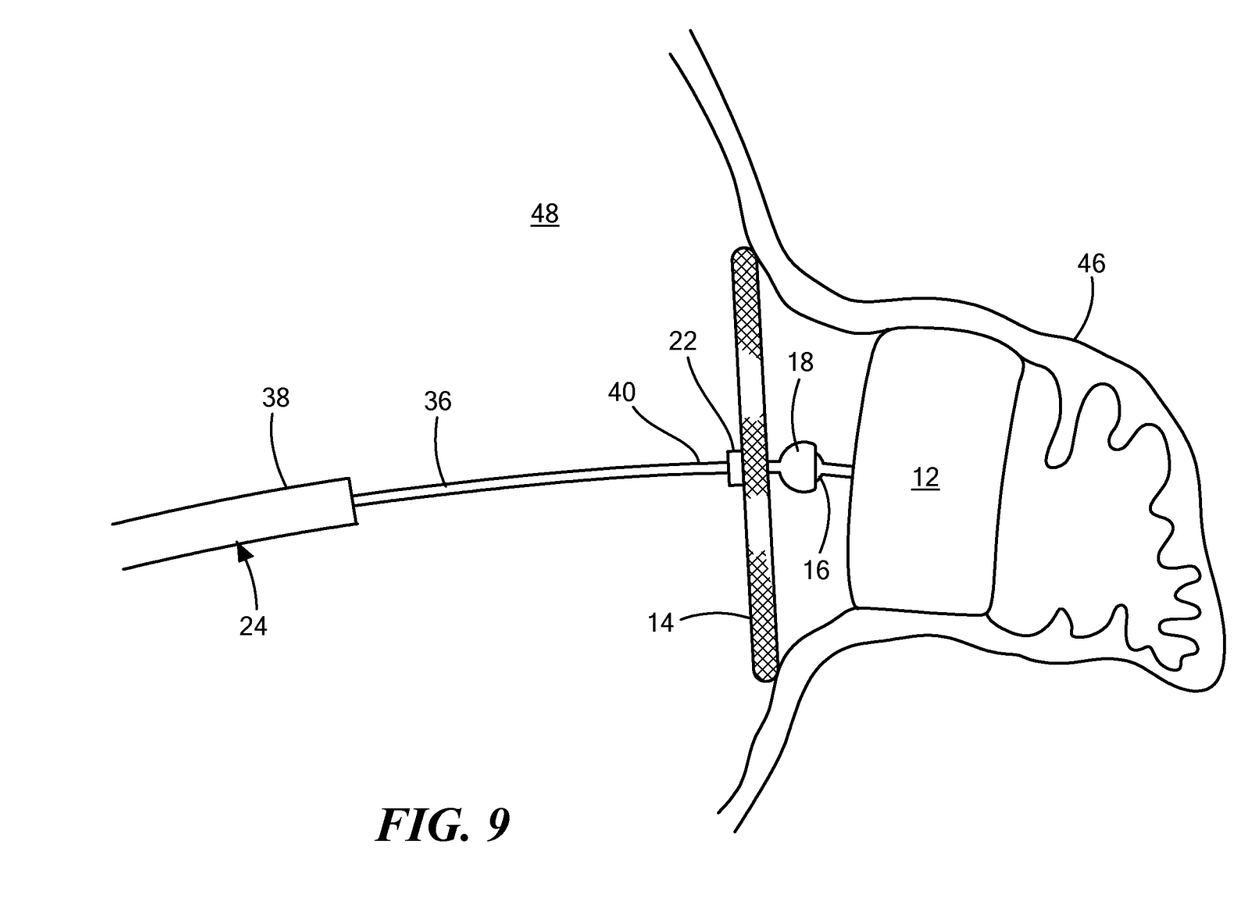
FIG. 9 is a further step in delivering the modular closure device to the target site in accordance with the present disclosure, wherein the modular closure device is in the fully expanded configuration at the target site.

Referring now to FIG. 9, the delivery device 24 is withdrawn away from the anchor element 12 and/or the push rod 36 is advanced through the delivery device 24 to cause the disc element 14 to emerge from the distal tip 40 of the delivery device 24. Once the disc element 14 is advanced distally from the delivery device 24, the disc element 14 may self expand, for example, in embodiments wherein the disc element 14 is composed of a shape memory material and/or if the disc element 14 is a mesh composed of a flexible and resilient material that is configured to expand after compression. In one embodiment, the size of the disc element 14 is chosen such that, when expanded, the disc element 14 has a diameter $D_{14}$ that is greater than a greatest diameter $D_{52}$ of the opening 52 of the LAA 46. Put another way, the size of the disc element 14 is chosen such that the disc element 14 prevents the flow of blood, or at least larger particles such as clots, from leaving the LAA 46 and entering the left atrium.

Referring now to FIG. 10, the push rod 36 is disengaged from the disc element 14 and the push rod 36 and delivery device 24 are removed from the patient's body. In one embodiment, a distal tip 40 of the push rod 36 is removably engaged with the engagement element 22 on the disc element 14. In one embodiment, the distal tip 40 and the engagement element 22 have complementary threading such that the push rod 36 may be screwed onto, and unscrewed from, the disc element 14. However, it will be understood that the distal tip 40 and engagement element 22 may have other suitable engagement mechanisms, such as snap fit, friction fit, clamps, hook and loop, ball and socket, or the like. In embodiments wherein the modular closure device 10 is configured such that the inflatable element 28 is removed after implantation of the modular closure device 10, this step also includes removal of the inflatable element 28.

EMBODIMENTS

In one embodiment, a medical device 10 comprises: an anchor element 12, the anchor element 12 including a first connection element 16; and a disc element 14, the disc element 14 including a second connection element 18 pivotably coupled to the first connection element 16, the anchor element 12 being sized to be received and retained within a left atrial appendage and the disc element 14 being sized to completely cover an opening of the left atrial appendage.

In one aspect of the embodiment, the first connection element 16 is a ball and the second connection element 18 is a socket that is configured to receive and retain at least a portion of the ball 16.

In one aspect of the embodiment, the anchor element 12 is a self-expanding frame 26.

In one aspect of the embodiment, the self-expanding frame 26 includes at least one of a mesh 32 and a plurality of arms 34. In one aspect of the embodiment, the self-expanding frame 26 includes a plurality of arms 34 and a mesh 32 at least partially surrounding the plurality of arms 34.

In one aspect of the embodiment, the self-expanding frame 26 is composed of a shape memory material.

In one aspect of the embodiment, the anchor element 12 includes: an expandable frame 30; and an inflatable element 28 within the expandable frame 30.

In one aspect of the embodiment, inflation of the inflatable element 28 expands the expandable frame 30.

In one aspect of the embodiment, the expandable frame 30 includes at least one of a mesh 32 and a plurality of arms 34.

In one aspect of the embodiment, the expandable frame 30 is composed of a shape memory material.

In one aspect of the embodiment, the disc element 14 is composed of a shape memory material.

In one aspect of the embodiment, the disc element 14 is composed of a resilient and flexible material.

In one aspect of the embodiment, the disc element 14 includes a threaded engagement element 22.

In one embodiment, a system for a left atrial appendage comprises: a modular closure device, the modular closure device including: an anchor element 12, the anchor element 12 including a ball 16 connected to the anchor element 12 by a post 20, the anchor element 12 including a self-expanding frame 26 composed of a shape memory material; and a disc element 14, the disc element 14 including a socket 18 that is pivotably couplable to the ball 16 of the anchor element 12 and an engagement element 22, the disc element 14 being composed of a shape memory material, the anchor element 12 being sized to be received and retained within a left atrial appendage and the disc element 14 being sized to completely cover an opening of the left atrial appendage; and a delivery device, the delivery device including a push rod that is removably couplable to the engagement element of the disc element. In one aspect of the embodiment, the self-expanding frame 26 includes a plurality of arms 34 and a mesh 32 covering at least a portion of the plurality of arms 34.

In one embodiment, a method for implanting a modular closure device 10 within a left atrial appendage 46 comprises: selecting an anchor element 12 based on the size and configuration of the left atrial appendage 46 of a patient, the anchor element 12 including a first connection element 16; selecting a disc element 14 based on the size and configuration of an opening of the left atrial appendage 46 of the patient, the disc element 14 including a second connection element 18; coupling the first connection element 16 of the anchor element 12 to the second connection element 18 of the disc element 14 to assemble the modular closure device 10; and compressing the modular closure device 10 and inserting the modular closure device 10 into a delivery device 24.

In one aspect of the embodiment, the method further comprises: inserting a distal end 38 of the delivery device 24 within the left atrial appendage 46; advancing the modular closure device 10 out of the distal end 38 of the delivery device 24 until the anchor element 12 is distal to the distal end 38 of the delivery device 24; expanding the anchor element 12 within the left atrial appendage 46 such that at least a portion of the anchor element 12 is in contact with an internal surface of the left atrial appendage 46; advancing the modular closure device 10 out of the distal end 38 of the delivery device 24 until the disc element 14 is distal to the distal end 38 of the delivery device 24; and expanding the disc element 14 such that the disc element 14 has an outer diameter $D_{14}$ that is greater than a largest diameter $D_{52}$ of an opening 52 of the left atrial appendage 46.

In one aspect of the embodiment, the anchor element 12 includes a self-expanding frame 26 composed of a shape memory material, and expanding the anchor element 12 includes allowing the self-expanding frame 26 to return to a programmed shape after compression.

In one aspect of the embodiment, the anchor element 12 includes an expandable frame 30 and an inflatable element 28 within the expandable frame 30, and expanding the anchor element 12 includes inflating the inflatable element 28 to expand the expandable frame 30.

In one aspect of the embodiment, the disc element 14 is composed of a shape memory material, and expanding the disc element 14 includes allowing the disc element 14 to return to a programmed shape after compression.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
   an anchor element, the anchor element having a self-expanding frame with a plurality of arms, each arm in the plurality of arms having a length, a first end and a second end opposite the first end, the first end being secured to the anchor element and the second end being a free end that is freely movable, the plurality of arms being interconnected at one or more locations along the length of each arm, the anchor element including a first connection element;
   a disc element, the disc element including a second connection element pivotably coupled to the first connection element; and
   the first connection element being a ball and the second connection element being a socket, the second connection element being configured to be removably connected to the first connection element such that other anchor elements are insertable into the socket,
   the anchor element being sized to be received and retained within a left atrial appendage and the disc element being sized to completely cover an opening of the left atrial appendage.

2. The medical device of claim 1, wherein the self-expanding frame further comprises a mesh and the plurality of arms has a first portion and a second portion, the mesh completely surrounding the first portion of the plurality of arms.

3. The medical device of claim 2, wherein the mesh has a plurality of protrusions for engaging a tissue.

4. The medical device of claim 1, wherein the self-expanding frame is composed of a shape memory material.

5. The medical device of claim 1, wherein the anchor element includes:
   an expandable frame; and
   an inflatable element within the expandable frame.

6. The medical device of claim 5, wherein inflation of the inflatable element expands the expandable frame.

7. The medical device of claim 5, wherein the expandable frame further includes a mesh and the plurality of arms has a first portion and a second portion, the mesh completely surrounding the first portion of the plurality of arms.

8. The medical device of claim 5, wherein the expandable frame is composed of a shape memory material.

9. The medical device of claim 1, wherein the disc element is composed of a shape memory material.

10. The medical device of claim 1, wherein the disc element is composed of a resilient and flexible material.

11. The medical device of claim 1, wherein the disc element includes a threaded engagement element.

12. The medical device of claim 1, wherein the disc element has a first surface and a second surface opposite the first surface, the first surface having an engagement element and the second surface having the second connecting element and a plurality of protrusions disposed on a mesh on the self-expanding frame wherein at least one of the plurality of protrusions is at least one barb.

13. A system for a left atrial appendage, the system comprising:
- a modular closure device, the modular closure device including:
  - an anchor element, the anchor element having a self-expanding frame with a plurality of arms, each arm in the plurality of arms having a length, a first end and a second end opposite the first end, the first end being secured to the anchor element and the second end being a free end that is freely movable, the plurality of arms being interconnected at more than one location along the length of each arm, the self-expanding frame being composed of a shape memory material, the anchor element including a ball connected to the anchor element by a post; and
  - a disc element, the disc element including a socket that is pivotably couplable to the ball of the anchor element and an engagement element, the socket of the disc element being removably connected to the ball of the anchor element such that other anchor elements are insertable into the socket, the disc element being composed of a shape memory material, the anchor element being sized to be received and retained within a left atrial appendage and the disc element being sized to completely cover an opening of the left atrial appendage; and
- a delivery device, the delivery device including a push rod that is removably couplable to the engagement element of the disc element.

14. The system of claim 13, wherein the self-expanding frame includes a mesh covering at least a portion of the plurality of arms.

15. The system of claim 14, wherein the mesh has a plurality of protrusions for engaging a tissue.

16. The system of claim 13, wherein the anchor element includes an inflatable element within the expandable frame.

17. The system of claim 16, wherein inflation of the inflatable element expands the expandable frame.

18. The System of claim 16, wherein the expandable frame further includes a mesh and the plurality of arms has a first portion and a second portion, the mesh completely surrounding the first portion of the plurality of arms.

19. The system of claim 18, wherein the mesh has a plurality of protrusions for engaging a tissue.

20. A medical device comprising:
- an anchor element, the anchor element having a self-expanding frame with a plurality of arms, each arm in the plurality of arms having a length, a first end and a second end opposite the first end, the first end being secured to the anchor element and the second end being a free end that is freely movable, the plurality of arms being interconnected at more than one location along the length of each arm, the anchor element including a first connection element;
- the self-expanding frame having a mesh and the plurality of arms having a first portion and a second portion, the mesh completely surrounding the first portion of the plurality of arms;
- the mesh having a plurality of protrusions for engaging a tissue;
- a disc element, the disc element including a second connection element pivotably coupled to the first connection element; and
- the first connection element being a ball and the second connection element being a socket, the second connection element being configured to be removably connected to the first connection element such that other anchor elements are insertable into the socket, the anchor element being sized to be received and retained within a left atrial appendage and the disc element being sized to completely cover an opening of the left atrial appendage.

* * * * *